(12) United States Patent
Moermann et al.

(10) Patent No.: US 10,180,502 B2
(45) Date of Patent: Jan. 15, 2019

(54) RADIOMETRIC DETECTOR FOR DETECTING A MEASUREMENT VARIABLE

(71) Applicant: Berthold Technologies GmbH & Co. KG, Bad Wildbad (DE)

(72) Inventors: Dirk Moermann, Bischweier (DE); Ewald Freiburger, Neulingen (DE); Steffen Mueller, Pforzheim (DE); Tobias Daibenzeiher, Neuenbuerg (DE)

(73) Assignee: Berthold Technologies GmbH & Co. KG, Bad Wildbad (DE)

( * ) Notice: Subject to any disclaimer, the term of this patent is extended or adjusted under 35 U.S.C. 154(b) by 0 days.

(21) Appl. No.: 15/877,023

(22) Filed: Jan. 22, 2018

(65) Prior Publication Data

US 2018/0143330 A1 May 24, 2018

Related U.S. Application Data

(63) Continuation of application No. 15/060,917, filed on Mar. 4, 2016, now Pat. No. 9,897,703.

(30) Foreign Application Priority Data

Mar. 5, 2015 (EP) .................................... 15157852

(51) Int. Cl.
*G01F 23/284* (2006.01)
*G01T 1/20* (2006.01)
*G01T 7/00* (2006.01)
*G01T 1/00* (2006.01)
*G01N 9/24* (2006.01)
*G01F 23/288* (2006.01)

(52) U.S. Cl.
CPC .......... *G01T 1/2006* (2013.01); *G01F 23/288* (2013.01); *G01N 9/24* (2013.01); *G01T 1/00* (2013.01); *G01T 1/2018* (2013.01); *G01T 7/005* (2013.01)

(58) Field of Classification Search
CPC . G01T 1/2006; G01T 1/00; G01T 7/00; G01F 23/288
USPC ...................................................... 250/357.1
See application file for complete search history.

(56) References Cited

U.S. PATENT DOCUMENTS

| 8,466,417 | B2 | 6/2013 | Rauer et al. |
| 8,569,683 | B2 | 10/2013 | Freiburger et al. |
| 8,604,414 | B2 * | 12/2013 | Rauer ................... G01F 23/288 250/252.1 |
| 2007/0278404 | A1 | 12/2007 | Spanke et al. |
| 2010/0140480 | A1 | 6/2010 | Rauer et al. |
| 2012/0085142 | A1 | 4/2012 | Rauer et al. |
| 2015/0338262 | A1 | 11/2015 | Glaser et al. |

FOREIGN PATENT DOCUMENTS

| DE | 101 32 267 A1 | 1/2003 |
| DE | 10 2004 007 680 A1 | 9/2005 |
| EP | 2 194 362 A1 | 6/2010 |
| EP | 2 378 312 A1 | 10/2011 |

* cited by examiner

*Primary Examiner* — David Porta
*Assistant Examiner* — Meenakshi Sahu
(74) *Attorney, Agent, or Firm* — Crowell & Moring LLP

(57) ABSTRACT

A radiometric detector is provided for detecting a measurement variable. The detector is particularly failsafe with, simultaneously, a simple, space-saving and cost-effective design, without having losses in the signal-to-noise ratio.

11 Claims, 2 Drawing Sheets

RADIOMETRIC DETECTOR FOR DETECTING A MEASUREMENT VARIABLE

CROSS REFERENCE TO RELATED APPLICATIONS

This application is a continuation of U.S. application Ser. No. 15/060,917, filed Mar. 4, 2016, which claims priority under 35 U.S.C. § 119 from European Patent Application No. 15157852.3, filed Mar. 5, 2015, the entire disclosures of which are herein expressly incorporated by reference.

BACKGROUND AND SUMMARY OF THE INVENTION

The invention relates to a radiometric detector for detecting a measurement variable.

Radiometric measurement systems, which comprise scintillation detectors for measuring radiation, are used in process metrology for measuring a measurement variable or a process variable such as e.g. a filling level, a moisture, a density, a mass flow, etc. By way of example, the scintillation detectors serve to determine the energy and/or intensity of ionizing radiation, wherein the energy and/or the intensity of the ionizing radiation depend(s) on the measurement variable.

In addition to the accuracy of the measurement of the measurement variable, a high availability of the measurement is important in process metrology. The absence of a measurement can lead to significant costs for the operator; in particular, damage to objects and persons may be the consequence in safety-critical installations.

The invention is based on the object of providing a radiometric detector for detecting a measurement variable, which detector is particularly failsafe while, simultaneously, having a simple design.

The invention achieves this object by the provision of a radiometric detector for detecting a measurement variable, comprising: a scintillator for generating light pulses, a plurality of optoelectronic sensors, wherein a respective optoelectronic sensor is embodied to convert the light pulses generated by the scintillator into an associated sensor signal; and an evaluation unit, comprising an assessment part, wherein the assessment part is embodied to assess a respective sensor signal as an error-free or erroneous sensor signal, and a summation part, wherein the summation part is embodied to form a summed sensor signal of the error-free sensor signals for the purposes of obtaining a measurement variable signal for the measurement variable.

The radiometric detector according to the invention for detecting a measurement variable has a scintillator for generating light pulses in a manner dependent on an incidence of ionizing radiation, wherein the radiation incidence is dependent on the measurement variable. In detail, the scintillator of the radiometric detector is excited when ionizing radiation passes through and it reemits the excitation energy in the form of light pulses. In particular, the scintillator can be a scintillation crystal.

Moreover, the radiometric detector has a plurality of optoelectronic sensors, wherein an optoelectronic sensor is embodied in each case to convert the light pulses generated by the scintillator into an associated electrical sensor signal. Hence, a plurality of sensor signals are generated. The sensor signals from the optoelectronic sensors are correlated in time since the scintillation light generated in the scintillator is distributed over all (or at least a multiplicity) of the optoelectronic sensors. The plurality of optoelectronic sensors are optically coupled to the scintillator; in particular, the optoelectronic sensors can be attached to the scintillator. The optoelectronic sensors can each have dedicated readout electronics, wherein the electrical sensor signals are formed and amplified in one of the readout electronics in each case. In particular, the optoelectronic sensors can be photomultipliers (electron tubes), photodiodes or silicon photomultipliers (SiPMs).

Moreover, the radiometric detector has an evaluation unit, wherein the respective sensor signals of the plurality of optoelectronic sensors are applied to the evaluation unit. The evaluation unit has an assessment part and a summation part. The assessment part is embodied to assess a respective sensor signal from the plurality of sensor signals as an error-free or erroneous sensor signal. Typically, a possible error or failure of one of the optoelectronic sensors causes a corresponding erroneous sensor signal. Hence, the assessment part can identify a possible error or failure of one of the optoelectronic sensors by assessing the respective sensor signals.

The summation part is embodied to form a summed sensor signal, preferably only, from only the error-free sensor signals for the purposes of obtaining a measurement variable signal for the measurement variable. Therefore, the individual sensor signals are evaluated in parallel. In the worst case, all sensor signals are assessed as erroneous sensor signals. No summed sensor signal is formed in that case. If the radiometric detector is fully functional, i.e. none of the optoelectronic sensors are faulty or failed and all sensor signals are assessed as error-free sensor signals, the best signal-to-noise ratio (S/N) is obtained by adding the time-correlated analogue sensor signals. This can be explained by virtue of the sensor signals being correlated in time (gamma event in the scintillator), but noise in each one of the individual optoelectronic sensors being temporally independent of the other sensors. Therefore, the sensor signals are processed in such a way that there are significant advantages and, in the worst case, no losses in the signal-to-noise ratio in relation to a single-sensor measurement system; i.e., there are no disadvantages from a metrological point of view.

The optoelectronic sensors therefore have an internally redundant embodiment. Typically, these have a higher failure probability than other components of the radiometric detector. Moreover, a voltage supply of the optoelectronic sensors can have a redundant and independent design. In the case of suitable mechanical encapsulation, the scintillator has a very low failure probability. Therefore, the radiometric detector can still establish a reliable summed sensor signal or a reliable measurement variable, even in the case of single sensor or multiple sensor failures. This increases the availability and reliability of the radiometric detector or the measurement and improves the characteristics within the scope of a functional safety consideration pursuant to SIL (safety integrity level). Since this is carried out in a single radiometric detector instead of by virtue of operating a plurality of radiometric measurement systems, this leads to significant savings for a customer during procurement, installation, operation and servicing of the radiometric detector. Moreover, the radiometric detector according to the invention saves space in relation to a plurality of radiometric measurement systems. This is advantageous in many applications, such as e.g. in the case of continuous casting in steelworks, in which the required space and the necessary power supply are likewise a limiting factor. The problem of a redundant radiometric detector lies in finding a compromise between granularity (degree of redundancy) and the best signal behaviour (formation of the analogue sum for highest S/N). The detector architecture presented here comprehensively enables both. Moreover, this is a particularly cost-effective variant as a result of using a single scintillator.

Alternatively, the radiometric detector according to the invention can have a multiplicity of scintillators arranged adjacent to one another, wherein at least one optoelectronic sensor is optically coupled to each scintillator. Each one of the plurality of scintillators with the at least one optoelectronic sensor can be referred to as a scintillation module. A plurality of these mutually independent scintillation modules are arranged packed together as closely as possible.

As described above, the assessment part in this variant is also embodied to assess a respective sensor signal from the plurality of sensor signals as error-free or erroneous sensor signal. In this case, the summation part is embodied to form individual summed sensor signals only from the error-free analogue sensor signals of the individual scintillation modules in each case and to form a summed sensor signal from the individual summed sensor signals or signals formed by further processing thereof for the purposes of obtaining a measurement variable signal for the measurement variable. As a result of an optical separation of the scintillation modules from one another, a time correlation between the analogue sensor signals from optoelectronic sensors of two different modules is only to be expected in the case of Compton scattering. The generated scintillation light or the generated light pulse remains within one scintillator and it is captured by the at least one optoelectronic sensor. Sensor signals not correlated in time may not be added in analogue form since this would otherwise reduce the S/N. All sensor signals or individual summed sensor signals are—at least averaged over time—linked linearly to one another if the radiometric detector is irradiated in a homogeneous fashion.

The use of a plurality of individual scintillators makes this variant more expensive but, on the other hand, increases the reliability of the radiometric detector since, for example, a break in the scintillator only affects the single scintillation module and the corresponding sensor signals.

In an embodiment of the invention, the scintillator, the plurality of optoelectronic sensors and the evaluation unit are arranged in a common housing. A customer or a user therefore receives a single device or a single object.

In an embodiment of the invention, the assessment part has a voting logic, such as a 1oo2 voting logic, wherein the voting logic is embodied to assess a respective sensor signal from the plurality of sensor signals as an error-free or erroneous sensor signal. A voting logic identifies errors or failures particularly well and quickly.

In an embodiment of the invention, the plurality of optoelectronic sensors has at least three optoelectronic sensors and the voting logic is embodied to compare the plurality of sensor signals to one another and to assess a respective sensor signal from the plurality of sensor signals as an error-free or erroneous sensor signal depending on the comparison result. In particular, this can be a 2oo3 voting logic. If the radiometric detector is fully functional, i.e. none of the optoelectronic sensors are faulty or failed, all sensor signals are—at least averaged over time, e.g. over 60 seconds—linearly linked to one another if the radiometric detector is irradiated in a homogeneous fashion. By way of example, if the fill level in a container drops, all (mean) sensor signals must increase by the same factor. If this is not the case and if deviations, e.g. by more than 10%, of one optoelectronic sensor from the other optoelectronic sensors are determined by comparing the sensor signals with each other, this indicates a malfunction or failure of the corresponding sensor or the corresponding scintillator. The corresponding sensor signal is then assessed as an erroneous sensor signal.

In an embodiment of the invention, the summation part has a switching element and a summation element. The switching element has a signal connection with the assessment part and it is embodied to forward a respective error-free sensor signal and not to forward a respective erroneous sensor signal. Forwarding or not forwarding a respective sensor signal can be carried out by appropriate switching states of switches of the switching element in a manner depending on the assessment of the assessment part. This renders it possible to mask an erroneous sensor signal from the summed sensor signal formation. The summation element is embodied to form the summed sensor signal from the error-free sensor signals forwarded by the switching element. As an alternative or in addition to the switching element, the summation part can have a correlator for signal processing.

In an embodiment of the invention, the evaluation unit has a comparator and a counter. The comparator is embodied to compare the summed sensor signal, or a signal formed by further processing of the summed sensor signal, with a measurement threshold and to generate an output signal depending on a comparison result. The comparator analyses the summed sensor signal or the signal formed by further processing of the summed sensor signal in terms of the height thereof. The output signal is generated if the signal height exceeds the measurement threshold. The counter is embodied to register the output signal and to generate a count rate signal for the purposes of obtaining the measurement variable signal for the measurement variable, wherein the count rate signal is a number of registered output signals per unit time. The count rate signal contains information about the measurement variable or process variable.

In an embodiment of the invention, the radiometric detector has an analogue-to-digital converter. The analogue-to-digital converter is embodied to digitize a respective sensor signal or the summed sensor signal or a signal formed by further processing of the summed sensor signal. In particular, the analogue-to-digital converter can be a constituent of the evaluation unit. The further procedure is then carried out digitally in the manner as described hereabove and herebelow. When digitizing the summed sensor signal by means of the analogue-to-digital converter, the comparator can be dispensed with if necessary. The evaluation unit, the analogue-to-digital converter, the assessment part, the summation part and/or the comparator can be realized in the form of a microprocessor and associated software.

Moreover, the evaluation unit can advantageously have a conversion part, wherein the conversion part is embodied to convert or transform the summed sensor signal or a signal formed by further processing of the summed sensor signal, such as the count rate signal, into the measurement variable signal for the measurement variable or process variable. In particular, to this end, conversion or transformation functions can be stored in the conversion part.

In an embodiment of the invention, the evaluation unit has a compensation part, wherein the compensation part has a signal connection with the assessment part. The compensation part is embodied to compensate a number of erroneous sensor signals during further processing of the summed sensor signal for the purposes of obtaining the measurement variable signal for the measurement variable. Here, the compensation part can advantageously be embodied to take into account an overall number of the plurality of optoelectronic sensors and hence of the sensor signals. By not taking into account an erroneous sensor signal, the latter is missing in the summed sensor signal, as a result of which an incorrect measurement variable signal may be caused. In the case of a specific number of erroneous sensor signals and a specific number of error-free sensor signals, the summed sensor signal can be reduced by a factor of number of error-free signals/overall number of the sensor signals (number of erroneous sensor signals plus number of error-free sensor signals) in relation to an expected summed sensor signal in the case of a fully functional detector. In particular, the height of the summed sensor signal or of a signal formed by further processing of the summed sensor signal may be so low that the signal level is no longer sufficient to exceed the measurement threshold of the counter. This then causes the count rate signal to equal zero. Advantageously, this is compensated for by the compensation part.

In an embodiment of the invention, the compensation part has an amplifier with an adjustable gain factor, wherein the amplifier has a signal connection with the assessment part. The amplifier is embodied to set the gain factor in a manner dependent on a number of error-free sensor signals and the number of erroneous sensor signals. Moreover, the amplifier is embodied to amplify the summed sensor signal with the gain factor for generating an amplified summed sensor signal or to attenuate the measurement threshold by the gain factor. Hence, the amplifier can compensate an erroneous sensor signal not considered when forming the summed sensor signal. In the case of a specific number of erroneous sensor signals and specific number of error-free sensor signals, the gain factor for amplifying the summed sensor signal is overall number of sensor signals/number of error-free signals. As a result, the height of the amplified summed sensor signal corresponds to an expected height of the summed sensor signal when there is no erroneous sensor signal in the radiometric detector. Additionally or alternatively, the measurement threshold of the comparator can advantageously be adjustable. Then, the gain factor for attenuating the measurement threshold is number of error-free signals/overall number of sensor signals. As a result, the summed sensor signal can exceed the attenuated measurement threshold and lead to the generation of an output signal.

In an embodiment of the invention, the radiometric detector has a malfunction output unit. The malfunction output unit has a signal connection with the assessment part and it is embodied to output a malfunction signal in the case of an erroneous sensor signal. The faulty behaviour or a failure of an individual optoelectronic sensor or a scintillator can be communicated immediately to a user or operator by means of the malfunction signal. Hence, servicing or repair of the affected component can take place before further components fail and hence the whole radiometric detector is no longer functional. In particular, the malfunction signal can contain information about the component that is faulty or failed. The malfunction signal can be output in acoustic form by means of a loudspeaker of the malfunction output unit, in optical form by means of at least one warning lamp of the malfunction output unit and/or in the form of an electronic communication to a control system for the radiometric detector or to a control centre.

Moreover, the radiometric detector can advantageously have a transmission part, wherein the transmission part is embodied to transmit the summed sensor signal or a signal formed by further processing of the summed sensor signal, such as the count rate signal or the measurement variable signal for the measurement variable or process variable, to an external device, for example in a control centre. In particular, the transmission part can be a modem or a signal transducer. For transmission purposes, use can be made of a bus system such as HART, Profibus, Modbus or EROA based on various physical carriers such as 4-20 mA, RS485 or FSK.

The respective constituents of the evaluation unit and also of the transmission part and all components required herefor, to the extent that they are present, have a failure risk which, in the most disadvantageous case, would lead to the transmission of an incorrect signal from the radiometric detector to e.g. a control centre.

In an embodiment of the invention, the radiometric detector has a further optoelectronic sensor, a comparison part and a further malfunction output unit. The further optoelectronic sensor is embodied to convert the light pulses generated by the scintillator into an associated further sensor signal. The comparison part is embodied to compare, in particular continuously, a further measurement variable signal formed by further processing of the further sensor signal with the measurement variable signal. Advantageously, the further measurement variable signal and the measurement variable signal can be applied to the comparison part. The further malfunction output unit is embodied to output a malfunction signal depending on a comparison result, for example in the case of a deviation of the further measurement variable signal from the measurement variable signal. In particular, the further malfunction output unit can have a signal connection with the comparison part. In particular, the further sensor signal of the further optoelectronic sensor may not be applied to the evaluation unit, to which the respective sensor signals of the plurality of optoelectronic sensors are applied. Instead, the radiometric detector can have a further evaluation unit for further processing of the further sensor signal to form the further measurement variable signal, wherein the further sensor signal from the further optoelectronic sensor may be applied to the further evaluation unit. Therefore, separate, further or completely independent signal generation and signal processing may take place. As a result of this, the comparison part can identify a possible fault or failure of the respective constituents of the evaluation unit, of the transmission part and/or of all components required herefor, to the extent that these are present, and it can output the malfunction signal by means of the further malfunction output unit, in particular communicate said malfunction signal to a user or operator. In particular, the malfunction signal may contain the information as to which part is faulty or failed. The malfunction signal can be output in acoustic form by means of a loudspeaker of the further malfunction output unit, in optical form by means of at least one warning lamp of the further malfunction output unit and/or in the form of an electronic communication to a control system for the radiometric detector or a control centre. Moreover, a transmission of the measurement variable signal from the radiometric detector to the outside can be interrupted in the case of a malfunction, for example by opening a switch of the radiometric detector.

In an embodiment of the invention, the measurement variable is a filling level or a moisture content or a density or a mass flow.

BRIEF DESCRIPTION OF THE DRAWINGS

Advantageous embodiments of the invention are depicted in the drawings and will be described below. In detail.

DETAILED DESCRIPTION OF THE DRAWINGS

Figure 1:
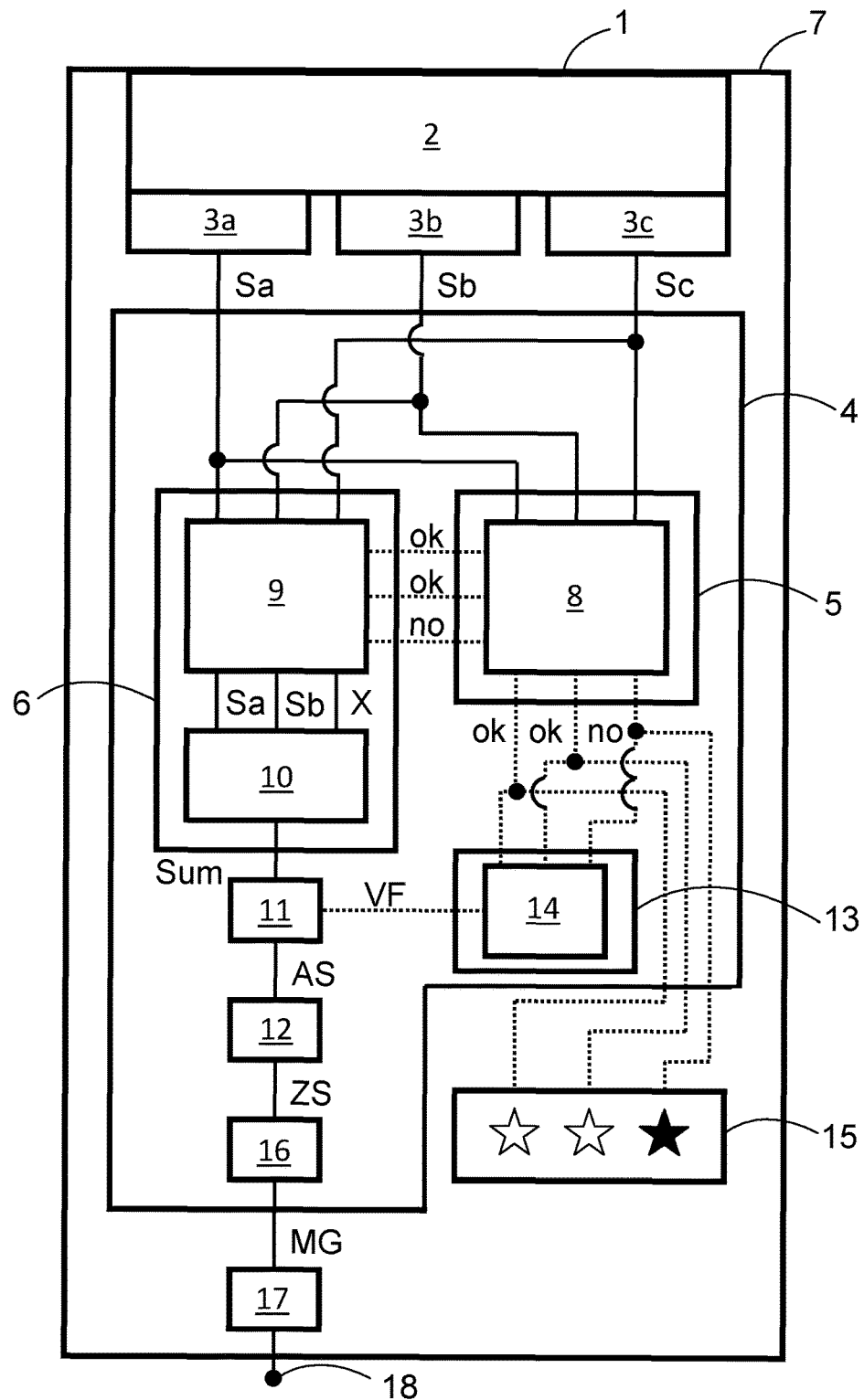
FIG. 1 shows a schematic block diagram of a radiometric detector according to the invention and FIG. 2 shows a schematic block diagram of a further radiometric detector according to the invention.

FIG. 1 shows a radiometric detector 1 with a housing 7. A scintillator 2, three optoelectronic sensors 3a, 3b, 3c, an evaluation unit 4 and a malfunction output unit 15 are arranged in the housing 7. Hence, the optoelectronic sensors 3a, 3b, 3c have an internally redundant embodiment. The optoelectronic sensors 3a, 3b, 3c are optically coupled to the scintillator 2, either directly or indirectly by way of at least one further element. In detail, they are applied to an inner side of the scintillator 2.

In the case of incidence of ionizing radiation, wherein the ionizing radiation depends on a measurement variable to be detected or to be measured, the scintillator 2 is excited and reemits the excitation energy in the form of light pulses. The optoelectronic sensors 3a, 3b, 3c are in each case embodied to convert the light pulses generated by the scintillator 2 into an associated electrical sensor signal Sa, Sb, Sc. Here, the sensor signals Sa, Sb, Sc from the optoelectronic sensors 3a, 3b, 3c are generally correlated in time since the scintillation light generated in the scintillator 2 is distributed over all of the optoelectronic sensors 3a, 3b, 3c. In the present case, the optoelectronic sensor 3c should be faulty and permanently output a sensor signal Sc equal to two, while the other optoelectronic sensors 3a, 3b are intended to be functional and output the sensor signals Sa, Sb with a value equal to one in each case only in the case of scintillation light.

The sensor signals Sa, Sb, Sc are applied to the evaluation unit 4, as indicated by the full lines in FIG. 1. The evaluation unit 4 has an assessment part 5 and a summation part 6. The assessment part 5 is embodied to assess a respective sensor signal Sa, Sb, Sc as an error-free or erroneous sensor signal. In detail, the assessment part has a voting logic 8 in the form of a 2oo3 voting logic, wherein the voting logic 8 is embodied to assess a respective sensor signal Sa, Sb, Sc as an error-free or erroneous sensor signal. The voting logic is embodied to compare the sensor signals Sa, Sb, Sc to one another and to assess a respective sensor signal Sa, Sb, Sc as an error-free or erroneous sensor signal depending on a comparison result. In the present case, the sensor signal Sc equals two and the other sensor signals Sa, Sb in each case equal one. By comparing the three sensor signals Sa, Sb, Sc to one another, the voting logic 8 identifies that the sensor signal Sc deviates from the other sensor signals Sa, Sb. Consequently, the voting logic 8 assesses the sensor signal Sc as erroneous (no) and the other sensor signals Sa, Sb as error-free (ok).

The summation part 6 is embodied to form a summed sensor signal Sum from only the error-free sensor signals Sa, Sb for the purposes of obtaining a measurement variable signal MG for the measurement variable. In detail, the summation part 6 has a switching element 9 and a summation element 10. The switching element 9 has a signal connection with the voting logic 8 of the assessment part 5, as indicated by the dotted lines in FIG. 1, and it is embodied to forward a respective error-free sensor signal Sa, Sb and not to forward a respective erroneous sensor signal Sc. Forwarding or not forwarding a respective sensor signal is carried out by appropriate switching states of switches in the switching element 9 in a manner depending on the assessment of the assessment part 5. In the present case, the error-free sensor signals Sa, Sb are forwarded to the summation element 10 while the erroneous sensor signal Sc is not forwarded to the to the summation element 10. The faulty sensor signal Sc is masked from the summed sensor signal formation.

The summation element 10 is embodied to form the summed sensor signal Sum from the error-free sensor signals Sa, Sb forwarded by the switching element 9. In detail, the summed sensor signal Sum is formed by adding the time correlated analogue sensor signals Sa, Sb; Sum=Sa+Sb. Hence, the individual sensor signals are evaluated in parallel.

Moreover, the evaluation unit has a comparator 11. The comparator 11 is embodied to compare the summed sensor signal Sum with an adjustable measurement threshold and to generate an output signal AS depending on a comparison result. The comparator 11 analyses the summed sensor signal Sum in terms of the height thereof. The output signal AS is generated if the signal height exceeds the measurement threshold. By way of example, the measurement threshold can be set to approximately 2.4 as a standard. Hence, in the case of three functional optoelectronic sensors 3a, 3b, 3c with three error-free sensor signals, each with a value of one, a summed sensor signal could equal three, as a result of which this would exceed the measurement threshold. In the present case, the summed sensor signal Sum equals two. Therefore, this would not exceed the threshold of 2.4 set as a standard. This would lead to an incorrect measurement variable signal MG since a light pulse in the scintillator caused or influenced by the measurement variable would not be taken into account.

However, the evaluation unit 4 has a compensation part 13, wherein the compensation part 13 has a signal connection with the assessment part 5, as indicated by the dotted lines in FIG. 1. The compensation part 13 is embodied to compensate a number of erroneous sensor signals when processing the summed sensor signal Sum further for the purposes of obtaining the measurement variable signal MG for the measurement variable. In detail, the compensation part 13 has an amplifier 14 with an adjustable gain factor VF, wherein the amplifier 14 has a signal connection with the assessment part 5. The amplifier 14 is embodied to set the gain factor VF in a manner dependent on a number of error-free sensor signals and the number of erroneous sensor signals. Moreover, the amplifier 14 has a signal connection with the comparator 11 and it is embodied to attenuate the measurement threshold of the comparator 11 by the gain factor VF. Therefore, the amplifier 14 can compensate an erroneous sensor signal not taken into account when forming the summed sensor signal. In the present case, the number of error-free sensor signals is two, Sa and Sb, and the number of erroneous sensor signals is one, Sc. The amplifier sets the gain factor VF to $2/3$. Hence, the measurement threshold is set to be 1.6. As a result, the summed sensor signal Sum formed from only two error-free sensor signals can exceed the attenuated measurement threshold and it leads to the generation of the output signal AS.

The evaluation unit has a counter 12. The counter 12 is embodied to register the output signal AS and to generate a count rate signal ZS for the purposes of obtaining the measurement variable signal MG for the measurement variable, wherein the count rate signal ZS is a number of registered output signals AS per unit time.

Moreover, the evaluation unit 4 has a conversion part 16, wherein the conversion part 16 is embodied to convert the count rate signal ZS into the measurement variable signal MG for the measurement variable, e.g. a fill level. A conversion function is stored in the conversion part 16.

Furthermore, the radiometric detector 1 has a transmission part 17 in the form of a modem or a signal transducer, wherein the transmission part 17 is embodied to transmit the measurement variable signal MG to an external device 18, for example in a control centre. For transmission purposes, use can be made of a bus system such as HART, Profibus, Modbus or EROA based on various physical carriers such as 4-20 mA, RS485 or FSK.

The shown radiometric detector 1 can consequently still establish a reliable summed sensor signal Sum or a reliable measurement variable signal MG, even in the case of a single-sensor failure.

Furthermore, the malfunction output unit 15 has a signal connection with the evaluation part 5, as indicated by the dotted lines in FIG. 1, and it is embodied to output a malfunction signal in the case of an erroneous sensor signal. In detail, the malfunction output unit 15 is embodied to output a malfunction signal for each one of the optoelectronic sensors 3a, 3b, 3c in optical form by way of three warning lamps. In the present case, the warning lamp for the optoelectronic sensor 3c outputs a malfunction signal.

Figure 2:
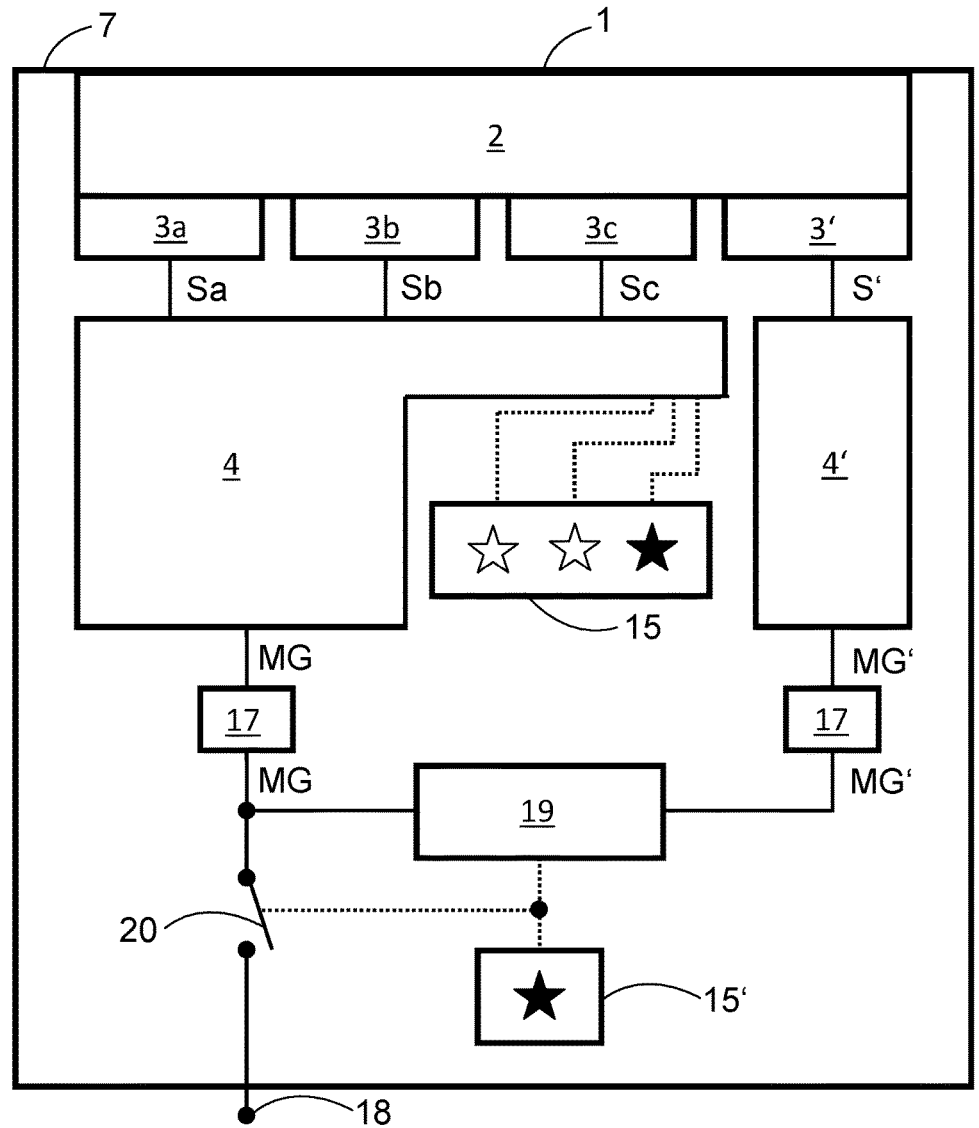

FIG. 2 shows a further embodiment for a further radiometric detector 1, wherein, for easier understanding, not only identical but also functionally equivalent elements have been provided with the same reference sign as in the embodiment explained above, with it being possible to refer to the description of said embodiment in this respect. In addition to the radiometric detector 1 from FIG. 1, the radiometric detector 1 from FIG. 2 has a further optoelectronic sensor 3', a comparison part 19 and a further malfunction output unit 15'. The further optoelectronic sensor 3' is embodied to convert the light pulses generated by the scintillator 2 into an associated further sensor signal S'. The comparison part 19 is embodied to compare, in particular continuously, a further measurement variable signal MG' formed by further processing of the further sensor signal S' with the measurement variable signal MG. The measurement variable signal MG after the transmission part 17 and the further measurement variable signal MG' after a further transmission part 17 are applied to the comparison part 19, as indicated by the full lines in FIG. 2. In detail, the radiometric detector 1 has a further evaluation unit 4' for processing the further sensor signal S' further to form the further measurement variable signal MG', wherein the further sensor signal S' of the further optoelectronic sensor 3' is applied to the further evaluation unit 4'. As a result, there is separate, further or completely independent signal generation and signal processing of the signal S' in relation to the signals Sa, Sb and Sc. The further evaluation unit 4' can differ in terms of the design thereof from the design of the evaluation unit 4. The further malfunction output unit 15' is embodied to output a malfunction signal in a manner dependent on a comparison result of the comparison part 19. The further malfunction output unit 15' has a signal connection with the comparison part 19, as shown by the dotted lines in FIG. 2. In detail, the malfunction output unit 15 is embodied to output a malfunction signal in optical form by way of a warning lamp.

In the present case, the conversion part 16 of the evaluation unit 4 is defect and the measurement variable signal MG equals zero, whereas the further evaluation unit 4' and the further transmission part 17 are functional and the further measurement variable signal MG' is different from zero. By comparison of the measurement variable signal MG with the further measurement variable signal MG', the comparison part 19 identifies that the measurement variable signal MG deviates from the further measurement variable signal MG'. Consequently, the warning lamp of the further malfunction output unit 15' outputs a malfunction signal. Moreover, the radiometric detector 1 has a switch 20. The switch 20 has a signal connection with the comparison part 19. In the case of a malfunction, as is present in this example, the switch 20 is opened. As a result, the transmission of the incorrect measurement variable signal MG from the radiometric detector 1 to the outside to the external device 18 is interrupted. Otherwise, the switch 20 can be closed and the measurement variable signal MG can be transmitted to the outside, to the extent that the measurement variable signal is error-free and there is no deviation from the further measurement variable signal MG'.

In the shown embodiments, the radiometric detector respectively has three and four optoelectronic sensors. Alternatively, it can have two or more than three or four optoelectronic sensors.

Moreover, the radiometric detector in the shown embodiments has a single scintillator. Alternatively, the radiometric detector can have a multiplicity of scintillators arranged adjacent to one another, wherein at least one optoelectronic sensor can be optically coupled to each scintillator. A plurality of these mutually independent scintillation modules can be arranged in the housing of the radiometric detector in a manner packed as densely as possible. In this case, the summation part can be embodied to form individual summed sensor signals from only the error-free analogue sensor signals from the individual scintillation modules in each case and to form a summed sensor signal from the individual summed sensor signals or from these signals formed by further processing thereof for the purposes of obtaining a measurement variable signal for the measurement variable.

Moreover, the amplifier is embodied to attenuate the measurement threshold by the gain factor. Alternatively, the amplifier can be embodied to amplify the summed sensor signal by the gain factor in order to generate an amplified summed sensor signal.

In the shown embodiments, the respective sensor signals and the summed sensor signal are analogue signals. Advantageously, the radiometric detector can have an analogue-to-digital converter, wherein the analogue-to-digital converter can be embodied to digitize a respective sensor signal or the summed sensor signal or a signal formed by further processing of the summed sensor signal. In particular, the analogue-to-digital converter can be a constituent of the evaluation unit. The further procedure is then carried out digitally in the manner described above. When digitizing the summed sensor signal by means of the analogue-to-digital converter, the comparator can be dispensed with if necessary. The evaluation unit, the analogue-to-digital converter, the evaluation part, the summation part and/or the comparator can be realized in the form of a microprocessor and associated software.

Additionally or alternatively to outputting a malfunction signal in optical form, the malfunction output unit and/or the further malfunction output unit can be embodied to output a malfunction signal in acoustic form by means of a loudspeaker and/or in the form of an electronic communication to a control system for the radiometric detector.

As the embodiments which were shown and explained above make clear, the invention provides an advantageous radiometric detector for detecting a measurement variable, wherein the detector is particularly failsafe with, simultaneously, a simple, space-saving and cost-effective design, without having losses in the signal-to-noise ratio.

What is claimed is:

1. A radiometric detector for detecting a measurement variable, comprising:
   a scintillator for generating light pulses;
   a plurality of optoelectronic sensors, wherein a respective optoelectronic sensor is embodied to convert the light pulses generated by the scintillator into an associated sensor signal; and
   an evaluation unit, comprising
      an assessment part, wherein the assessment part is embodied to assess a respective sensor signal as an error-free or erroneous sensor signal, and
      a summation part, wherein the summation part is embodied to form a summed sensor signal only of the error-free sensor signals for the purposes of obtaining a measurement variable signal for the measurement variable.

2. The radiometric detector according to claim 1, wherein the scintillator, the plurality of optoelectronic sensors and the evaluation unit are arranged in a common housing.

3. The radiometric detector according to claim 1, wherein the assessment part comprises a voting logic, wherein the voting logic is embodied to assess a respective sensor signal as an error-free or erroneous sensor signal.

4. The radiometric detector according to claim 3, wherein the plurality of optoelectronic sensors comprises at least three optoelectronic sensors and the voting logic is embodied to compare the plurality of sensor signals to one another and to assess a respective sensor signal as an error-free or erroneous sensor signal depending on a comparison result.

5. The radiometric detector according to claim 1, wherein the summation part comprises:
   a switching element, wherein the switching element has a signal connection with the assessment part and the switching element is embodied to forward a respective error-free sensor signal and not to forward a respective erroneous sensor signal, and
   a summation element, wherein the summation element is embodied to form the summed sensor signal from the error-free sensor signals forwarded by the switching element.

6. The radiometric detector according to claim 1, wherein the evaluation unit comprises:
   a comparator, wherein the comparator is embodied to compare the summed sensor signal, or a signal formed by further processing of the summed sensor signal, with a measurement threshold and to generate an output signal depending on a comparison result, and
   a counter, wherein the counter is embodied to register the output signal and to generate a count rate signal for the purposes of obtaining the measurement variable signal for the measurement variable, wherein the count rate signal is a number of registered output signals per unit time.

7. The radiometric detector according to claim 1, further comprising an analogue-to-digital converter, wherein the analogue-to-digital converter is embodied to digitize a respective sensor signal or the summed sensor signal or a signal formed by further processing of the summed sensor signal.

8. The radiometric detector according to claim 1, wherein the evaluation unit comprises a compensation part, wherein the compensation part has a signal connection with the assessment part and the compensation part is embodied to compensate a number of erroneous sensor signals during further processing of the summed sensor signal for the purposes of obtaining the measurement variable signal for the measurement variable.

9. The radiometric detector according to claim 1, further comprising a malfunction output unit, wherein the malfunction output unit has a signal connection with the assessment part and the malfunction output unit is embodied to output a malfunction signal in the case of an erroneous sensor signal.

10. The radiometric detector according to claim 1, further comprising a further optoelectronic sensor, a comparison part and a malfunction output unit, wherein the further optoelectronic sensor is embodied to convert the light pulses generated by the scintillator into an associated further sensor signal, wherein the comparison part is embodied to compare a further measurement variable signal formed by further processing of the further sensor signal with the measurement variable signal and wherein the malfunction output unit is embodied to output a malfunction signal depending on a comparison result.

11. The radiometric detector according to claim 1, wherein the measurement variable is a filling level, a moisture content, a density or a mass flow.

* * * * *